United States Patent
Joyabu et al.

(10) Patent No.: US 11,578,028 B2
(45) Date of Patent: Feb. 14, 2023

(54) SURFACTANT COMPOSITION

(71) Applicant: DAI-ICHI KOGYO SEIYAKU CO., LTD., Kyoto (JP)

(72) Inventors: Masatake Joyabu, Kyoto (JP); Kei Shiohara, Kyoto (JP); Asako Ogasawara, Kyoto (JP); Takuro Kimura, Kyoto (JP); Chi Tao, Kyoto (JP)

(73) Assignee: DAI-ICHI KOGYO SEIYAKU CO., LTD., Kyoto (JP)

( * ) Notice: Subject to any disclaimer, the term of this patent is extended or adjusted under 35 U.S.C. 154(b) by 943 days.

(21) Appl. No.: 16/334,589

(22) PCT Filed: Aug. 22, 2017

(86) PCT No.: PCT/JP2017/029969
§ 371 (c)(1),
(2) Date: Mar. 19, 2019

(87) PCT Pub. No.: WO2018/061532
PCT Pub. Date: Apr. 5, 2018

(65) Prior Publication Data
US 2020/0331830 A1    Oct. 22, 2020

(30) Foreign Application Priority Data
Sep. 29, 2016    (JP) .............. JP2016-191119

(51) Int. Cl.
| | | |
|---|---|---|
| C07C 33/30 | (2006.01) | |
| C07C 43/166 | (2006.01) | |
| C08F 2/26 | (2006.01) | |
| C08F 2/30 | (2006.01) | |
| C08F 216/10 | (2006.01) | |
| C08F 12/08 | (2006.01) | |
| C08F 20/06 | (2006.01) | |
| C08F 20/18 | (2006.01) | |
| C08K 5/06 | (2006.01) | |

(52) U.S. Cl.
CPC .............. *C07C 43/166* (2013.01); *C08F 2/26* (2013.01); *C08F 12/08* (2013.01); *C08F 20/06* (2013.01); *C08F 20/18* (2013.01); *C08K 5/06* (2013.01); *C07C 33/30* (2013.01); *C08F 216/10* (2013.01)

(58) Field of Classification Search
None
See application file for complete search history.

(56) References Cited

U.S. PATENT DOCUMENTS

| | | | |
|---|---|---|---|
| 9,637,563 B2 * | 5/2017 | Ogasawara | ............... C08F 2/24 |
| 2014/0323753 A1 | 10/2014 | Ogasawara et al. | |
| 2015/0011790 A1 | 1/2015 | Ogasawara et al. | |
| 2016/0137755 A1 * | 5/2016 | Ogasawara | ............ C09K 23/14 |
| | | | 252/182.17 |

FOREIGN PATENT DOCUMENTS

| | | | | |
|---|---|---|---|---|
| WO | WO 2013/108588 A1 | 7/2013 | | |
| WO | WO 2015/001968 A1 | 1/2015 | | |
| WO | WO-2015001968 A1 * | 1/2015 | .......... B01F 17/0021 |

OTHER PUBLICATIONS

International Search Report dated Nov. 28, 2017 in PCT/JP2017/029969 filed Aug. 22, 2017.

* cited by examiner

*Primary Examiner* — Richard A Huhn
(74) *Attorney, Agent, or Firm* — Oblon, McClelland, Maier & Neustadt, L.L.P.

(57) ABSTRACT

The polymerization stability and the chemical stability and the water resistance of resin films are improved. A surfactant composition according to an embodiment contains a surfactant (A) represented by general formula (1) and an anionic surfactant (B) having a hydrophobic group different from that of the surfactant (A). In the formula, $R^1$ represents one or two groups selected from groups below, $D^1$ represents a polymerizable unsaturated group represented by chemical formula $D^1$-1 or $D^1$-2 below, $R^2$ represents a hydrogen atom or a methyl group, m1 and m2 represent 1 to 2, $A^1$ represents an alkylene group with 2 to 4 carbon atoms, and m3 represents 1 to 100.

[Chem. 1]

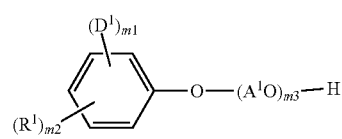

(1)

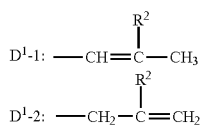

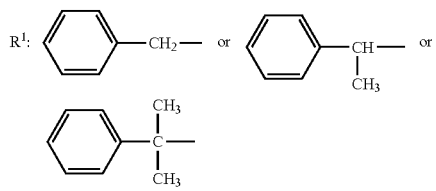

5 Claims, No Drawings

SURFACTANT COMPOSITION

TECHNICAL FIELD

Embodiments of the present invention relate to a surfactant composition and a method for producing an aqueous resin dispersion using the surfactant composition.

BACKGROUND ART

Aqueous resin dispersions produced by emulsion polymerization are used as, for example, various coating materials such as water-based paints, gluing agents, adhesives, and binders for paper processing. In emulsion polymerization, an anionic or nonionic surfactant is used as an emulsifier for monomers and a dispersant for produced resins. In general, an anionic surfactant exhibits high polymerization stability, but has insufficient chemical stability. On the other hand, a nonionic surfactant exhibits high chemical stability, but has insufficient polymerization stability. Therefore, a mixture of an anionic surfactant and a nonionic surfactant is used in the production of aqueous resin dispersions required to have high chemical stability.

However, when the surfactant used is a nonreactive surfactant, a resin film obtained from such an aqueous resin dispersion has insufficient water resistance. To address this problem, PTL 1 and PTL 2 propose a method that uses a reactive surfactant and PTL 3 proposes a method that uses a reactive surfactant and an acrylamide monomer in combination. However, sufficient polymerization stability and water resistance are not satisfied in these inventions.

CITATION LIST

Patent Literature

PTL 1: Japanese Unexamined Patent Application Publication No. 2002-97212
PTL 2: Japanese Unexamined Patent Application Publication No. 2003-268021
PTL 3: Japanese Unexamined Patent Application Publication No. 2004-292749
PTL 4: WO2013/108588A1
PTL 5: Japanese Unexamined Patent Application Publication No. 2015-13921

SUMMARY OF INVENTION

Technical Problem

As described above, it is difficult to simultaneously satisfies three characteristics, namely, the polymerization stability, the chemical stability, and the water resistance of resin films. Thus, the surfactants in the related art need to be further improved.

In view of the foregoing, it is an object of embodiments of the present invention to provide a surfactant composition that can contribute to production of an aqueous resin dispersion which has high polymerization stability and high chemical stability and which provides a resin film with high water resistance.

Solution to Problem

A surfactant composition according to this embodiment contains a surfactant (A) represented by general formula (1) below and an anionic surfactant (B) having a hydrophobic group different from that of the surfactant (A).

[Chem. 1]

$$(D^1)_{m1} \text{—Ar—} O\text{—}(A^1O)_{m3}\text{—}H \quad (R^1)_{m2} \tag{1}$$

In the formula (1), $D^1$ represents a polymerizable unsaturated group represented by chemical formula $D^1$-1 or $D^1$-2 below, $R^2$ in the formulae represents a hydrogen atom or a methyl group, $R^1$ represents one or two groups selected from groups below, $m1$ and $m2$ each represent 1 to 2 on average in an entirety of the surfactant (A), $A^1$ represents an alkylene group with 2 to 4 carbon atoms, and $m3$ representing an average number of moles of an oxyalkylene group added represents 1 to 100.

[Chem. 2]

$$D^1\text{-1: } -CH=\underset{R^2}{C}-CH_3$$

$$D^1\text{-2: } -CH_2-\underset{R^2}{C}=CH_2$$

[Chem. 3]

$$R^1: \text{Ph—}CH_2\text{—} \quad \text{or} \quad \text{Ph—}\underset{CH_3}{CH}\text{—} \quad \text{or} \quad \text{Ph—}\underset{CH_3}{\overset{CH_3}{C}}\text{—}$$

In one embodiment, the anionic surfactant (B) preferably has a polymerizable carbon-carbon unsaturated bond.

The anionic surfactant (B) preferably has at least one hydrophobic group selected from the group consisting of a styrenated phenyl group, an alkyl group with 10 to 18 carbon atoms, an alkenyl group with 16 to 18 carbon atoms, a 1-(allyloxymethyl)alkyl group, and an alkylpropenylphenyl group.

The anionic surfactant (B) is preferably at least one anionic surfactant selected from the group consisting of polyoxyalkylene styrenated phenyl ether sulfates, polyoxyalkylene styrenated phenyl ether phosphates, polyoxyalkylene styrenated phenyl ether carboxylates, polyoxyalkylene styrenated phenyl ether sulfosuccinates, polyoxyalkylene alkyl ether sulfates, polyoxyalkylene alkyl ether phosphates, polyoxyalkylene alkyl ether carboxylates, polyoxyalkylene alkyl ether sulfosuccinates, polyoxyalkylene alkenyl ether sulfates, polyoxyalkylene alkenyl ether phosphates, polyoxyalkylene alkenyl ether carboxylates, polyoxyalkylene alkenyl ether sulfosuccinates, polyoxyalkylene styrenated propenylphenyl ether sulfates, polyoxyalkylene styrenated propenylphenyl ether phosphates, polyoxyalkylene styrenated propenylphenyl ether carboxylates, polyoxyalkylene styrenated propenylphenyl ether sulfosuccinates, polyoxyalkylene alkylpropenylphenyl ether sulfates, polyoxyalkylene alkylpropenylphenyl ether phosphates, polyoxyalkylene alkylpropenylphenyl ether carboxylates, and polyoxyalkylene alkylpropenylphenyl ether sulfosuccinates.

A method for producing an aqueous resin dispersion according to this embodiment includes polymerizing a polymerizable compound in water in the presence of the surfactant composition.

Advantageous Effects of Invention

According to this embodiment, there can be provided an aqueous resin dispersion that has high polymerization stability and high chemical stability and that provides a resin film with high water resistance.

DESCRIPTION OF EMBODIMENTS

Hereafter, embodiments of the present invention will be described in detail.
[Surfactant (A)]
A surfactant (A) used in this embodiment is a reactive nonionic surfactant and is represented by general formula (1) below.

[Chem. 4]

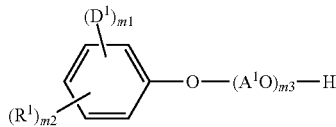
(1)

In the general formula (1), $D^1$ represents a polymerizable unsaturated group represented by chemical formula $D^1$-1 or $D^1$-2 below. When a plurality of groups $D^1$ are contained in one molecule, they may be the same as or different from each other. The entire surfactant (A) may also be constituted by compounds each having the same group $D^1$ or may also be a mixture of compounds having different groups $D^1$.

[Chem. 5]

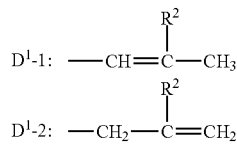

$R^2$ in the chemical formulae $D^1$-1 and $D^1$-2 represents a hydrogen atom or a methyl group. Therefore, $D^1$ specifically represents a 1-propenyl group, a 2-methyl-1-propenyl group, or a (meth)allyl group. $D^1$ may represent any one of the 1-propenyl group, the 2-methyl-1-propenyl group, and the (meth)allyl group or may represent a mixture of the 1-propenyl group, the 2-methyl-1-propenyl group, and the (meth)allyl group. $D^1$ preferably represents a 1-propenyl group. The (meth)allyl group refers to an allyl group and/or a methallyl group.

The number m1 of groups $D^1$ substituted is in the range of 1 to 2 on average in the entirety of the surfactant (A). From the viewpoint of polymerization stability, the number m1 preferably satisfies $1 < m1 < 1.5$. The molar ratio $(D^1$-1)/$(D^1$-2) of the group represented by the chemical formula $D^1$-1 to the group represented by the chemical formula $D^1$-2 is preferably more than 2. The substitution position of $D^1$ is preferably an ortho position and/or a para position and more preferably an ortho position.

In the general formula (1), $R^1$ represents one or two groups selected from groups below. When a plurality of groups $R^1$ are contained in one molecule, they may be the same as or different from each other. The entire surfactant (A) may also be constituted by compounds each having the same group $R^1$ or may also be a mixture of compounds having different groups $R^1$.

[Chem. 6]

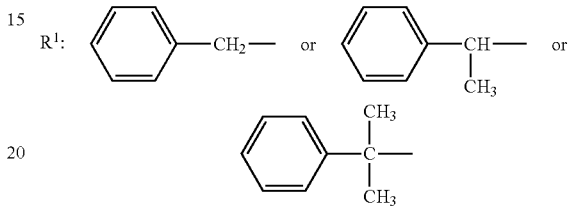

The number m2 of groups $R^1$ substituted is in the range of 1 to 2 on average in the entirety of the surfactant (A). The number m2 preferably satisfies $1 < m2 < 1.5$. The sum of the numbers m1 and m2 is preferably 3 or less and more preferably $2 < m1+m2 < 3$. The substitution position of $R^1$ is preferably an ortho position and/or a para position.

$A^1$ in the general formula (1) represents an alkylene group with 2 to 4 carbon atoms (i.e., alkanediyl group) and may represent a linear group or a branched group. Therefore, examples of the oxyalkylene group represented by $A^1O$ include an oxyethylene group, an oxypropylene group, and an oxybutylene group. An $(A^1O)_{m3}$ chain moiety in the general formula (1) is an addition polymer constituted by one or more alkylene oxides with 2 to 4 carbon atoms, such as ethylene oxide, propylene oxide, butylene oxide, and tetrahydrofuran (1,4-butylene oxide). The addition form of the oxyalkylene group is not particularly limited. A single adduct constituted by one alkylene oxide or a random or block adduct constituted by two or more alkylene oxides may be employed. Alternatively, the random adduct and the block adduct may be combined with each other.

The oxyalkylene group is particularly preferably an oxyethylene group. When two or more oxyalkylene groups are selected, one of the oxyalkylene groups is preferably an oxyethylene group. The $(A^1O)_{m3}$ chain moiety is a (poly) oxyalkylene chain preferably containing 50 to 100 mol % of an oxyethylene group and more preferably containing 70 to 100 mol % of an oxyethylene group.

Herein, m3 representing the average number of moles of the oxyalkylene group added is in the range of 1 to 100, preferably 5 to 80, and more preferably 10 to 50.

The method for producing the surfactant (A) represented by the general formula (1) is not particularly limited. The surfactant (A) is produced by, for example, a method described in paragraphs 0020 to 0025 in PTL 4 or a method described in paragraphs 0024 to 0027 in PTL 5.
[Anionic Surfactant (B)]
The anionic surfactant (B) used in this embodiment is an anionic surfactant having a hydrophobic group different from that of the surfactant (A). That is, the surfactant (B) is an anionic surfactant that does not have a hydrophobic group represented by formula (2) below and that has a hydrophobic group other than the hydrophobic group represented by the formula (2). Herein, $D^1$, $R^1$, m1, and m2 in the formula (2) are the same as $D^1$, $R^1$, m1, and m2 in the formula (1).

[Chem. 7]

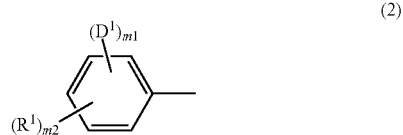

(2)

Although the mechanism is unclear, it is assumed that, by using the anionic surfactant (B) having a hydrophobic group different from that of the surfactant (A), these surfactants complement each other during polymerization that is caused in a dynamic environment such as physical agitation or movement of monomers in water, which improves the emulsification stability and the dispersion stability. Therefore, an aqueous resin dispersion that has high polymerization stability and high chemical stability and that provides a resin film with high water resistance can be provided.

The anionic surfactant (B) preferably has at least one hydrophobic group selected from the group consisting of, for example, a styrenated phenyl group, an alkyl group with 10 to 18 carbon atoms, an alkenyl group with 16 to 18 carbon atoms, a 1-(allyloxymethyl)alkyl group, and an alkylpropenylphenyl group.

Examples of the anionic surfactant having a styrenated phenyl group as a hydrophobic group include polyoxyalkylene styrenated phenyl ether sulfates, phosphates, carboxylates, and sulfosuccinates. The anionic surfactant is preferably a polyoxyalkylene styrenated phenyl ether sulfate and more preferably a polyoxyethylene styrenated phenyl ether sulfate.

Examples of the anionic surfactant having an alkyl group with 10 to 18 carbon atoms as a hydrophobic group include polyoxyalkylene alkyl ether sulfates, phosphates, carboxylates, and sulfosuccinates. The anionic surfactant is preferably a polyoxyalkylene alkyl ether sulfate and more preferably a polyoxyethylene alkyl ether sulfate. The number of carbon atoms of the alkyl group is more preferably 12 to 14.

Examples of the anionic surfactant having an alkenyl group with 16 to 18 carbon atoms as a hydrophobic group include polyoxyalkylene alkenyl ether sulfates, phosphates, carboxylates, and sulfosuccinates. The anionic surfactant is preferably a polyoxyalkylene alkenyl ether sulfate and more preferably a polyoxyethylene alkenyl ether sulfate. The number of carbon atoms of the alkenyl group is more preferably 18.

Examples of the anionic surfactant having a 1-(allyloxymethyl)alkyl group as a hydrophobic group include polyoxyalkylene-1-(allyloxymethyl)alkyl ether sulfates, phosphates, carboxylates, and sulfosuccinates. The anionic surfactant is preferably a polyoxyalkylene-1-(allyloxymethyl)alkyl ether sulfate and more preferably a polyoxyethylene-1-(allyloxymethyl)alkyl ether sulfate. The number of carbon atoms of the alkyl group is preferably 10 to 12.

Examples of the anionic surfactant having an alkylpropenylphenyl group as a hydrophobic group include polyoxyalkylene alkylpropenylphenyl ether sulfates, phosphates, carboxylates, and sulfosuccinates. The anionic surfactant is preferably a polyoxyalkylene alkylpropenylphenyl ether sulfate and more preferably a polyoxyethylene alkylpropenylphenyl ether sulfate. The number of carbon atoms of the alkyl group is preferably 8 to 12.

For the polyoxyalkylene chain in the specific examples of the anionic surfactant (B), the oxyalkylene group is an oxyalkylene group with 2 to 4 carbon atoms, such as an oxyethylene group, an oxypropylene group, or an oxybutylene group, and is preferably an oxyethylene group. The addition form of the oxyalkylene group is not particularly limited. A single adduct may be employed or a random or block adduct constituted by two or more alkylene oxides may be employed. The average number of moles of the oxyalkylene group added may be 1 to 100, 5 to 80, or 10 to 50. The polyoxyalkylene chain preferably contains 50 to 100 mol % of the oxyethylene group and more preferably contains 70 to 100 mol % of the oxyethylene group. The salt for an anionic hydrophilic group of the anionic surfactant (B) is, for example, an alkali metal salt, an alkaline-earth metal salt, an ammonium salt, or an alkanolamine salt (e.g., ethanol amine salt) and preferably an alkali metal salt such as a sodium salt or a potassium salt or an ammonium salt.

The anionic surfactant (B) preferably has a polymerizable carbon-carbon unsaturated bond, more specifically, a radically polymerizable unsaturated bond. By using such an anionic surfactant (B) having a polymerizable unsaturated bond in a combined manner, the water resistance of resin films can be further improved. Non-limiting examples of the group having a polymerizable carbon-carbon unsaturated bond include a 1-propenyl group, a 2-methyl-1-propenyl group, and a (meth)allyl group.

For the anionic surfactant (B), the above anionic surfactants may be used alone or in combination of two or more.

[Surfactant Composition]

The surfactant composition according to this embodiment contains the surfactant (A) and the anionic surfactant (B). The ratio of the surfactants, that is, the ratio (A/B) of the surfactant (A) to the anionic surfactant (B) is not particularly limited. The ratio is preferably A/B=6/4 to 1/9 and more preferably A/B=5/5 to 2/8 or may be A/B=4/6 to 2/8 on a mass basis.

The surfactant composition according to this embodiment can be used as an emulsifier for emulsion polymerization in which known reactive surfactants are used, an emulsifier for suspension polymerization, a resin modifier (e.g., improvement in water repellency, adjustment of hydrophilicity, improvement in compatibility, improvement in antistatic properties, improvement in antifogging properties, improvement in water resistance, improvement in adhesiveness, improvement in dyeing properties, improvement in film-forming properties, improvement in weather resistance, and improvement in blocking resistance), and a fiber treatment agent.

[Method for Producing Aqueous Resin Dispersion]

The method for producing an aqueous resin dispersion according to this embodiment is a method in which a polymerizable compound (hereafter referred to as a monomer) is polymerized in water in the presence of the surfactant composition. The polymerization method may be either emulsion polymerization or suspension polymerization. Hereafter, emulsion polymerization that is a preferred embodiment will be described in detail.

The emulsion polymerization can be performed by any publicly known method. The method can be appropriately selected from, for example, a batch polymerization method, a monomer dropping method, an emulsion dropping method, a seeded polymerization method, a multistage polymerization method, and a power-feed polymerization method, which are classified on the basis of the method for charging monomers. Non-limiting examples of a polymerization initiator used include hydrogen peroxide, ammonium persulfate, potassium persulfate, azobisisobutyronitrile, and benzoyl peroxide. Examples of a polymerization promoter that can be used include sodium hydrogen sulfite or ferrous ammonium sulfate. Examples of a chain transfer agent that may be used include α-methylstyrene dimers, mercaptans such as n-butyl mercaptan and t-dodecylmercaptan, and halogenated hydrocarbons such as carbon tetrachloride and carbon tetrabromide.

The monomer applied to the emulsion polymerization is not particularly limited and is applicable to various emulsions. For example, the monomer can be used for producing aqueous resin dispersions such as (meth)acrylate emulsion, styrene emulsion, vinyl acetate emulsion, halogenated olefin emulsion, SBR (styrene/butadiene) emulsion, ABS (acrylonitrile/butadiene/styrene) emulsion, BR (butadiene) emulsion, IR (isoprene) emulsion, and NBR (acrylonitrile/butadiene) emulsion. Two or more monomers may be mixed to perform emulsion polymerization.

The monomer for (meth)acrylate emulsion is, for example, (meth)acrylic acid and/or (meth)acrylate. Furthermore, (meth)acrylic acid and/or (meth)acrylate may be combined with other monomers (e.g., styrene, vinyl acetate, acrylonitrile, butadiene, vinylidene chloride, allylamine, vinylpyridine, (meth)acrylic acid alkylolamide, N,N-dimethylaminoethyl (meth) acrylate, and N,N-diethylaminoethyl vinyl ether). Herein, the (meth)acrylic acid refers to acrylic acid and/or methacrylic acid, and the (meth)acrylate refers to acrylate and/or methacrylate.

The monomer for styrene emulsion is styrene. Furthermore, styrene may be combined with other monomers (e.g., acrylonitrile, butadiene, fumaronitrile, maleinitrile, cyanoacrylate, phenylvinyl acetate, chloromethylstyrene, dichlorostyrene, vinylcarbazole, N,N-diphenylacrylamide, methylstyrene, and maleic acid).

The monomer for vinyl acetate emulsion is vinyl acetate. Furthermore, vinyl acetate may be combined with other monomers (e.g., styrene, vinyl chloride, acrylonitrile, maleic acid, maleate, fumaric acid, fumarate, ethylene, propylene, isobutylene, vinylidene chloride, cyclopentadiene, crotonic acid, acrolein, and alkyl vinyl ethers).

The monomer for halogenated olefin emulsion is vinyl chloride and/or vinylidene chloride. Furthermore, vinyl chloride and/or vinylidene chloride may be combined with other monomers (e.g., maleic acid, maleate, fumaric acid, fumarate, vinyl acetate, and vinyl benzoate).

For the amount of the surfactant composition according to this embodiment used, the total amount of the surfactant (A) and the anionic surfactant (B) is preferably 0.1 to 20 parts by mass and more preferably 0.2 to 10 parts by mass or may be 0.5 to 5 parts by mass relative to 100 parts by mass of the monomer.

In order to improve the polymerization stability during emulsion polymerization, a publicly known protective colloid can be used together. Examples of the protective colloid that can be used together include completely saponified polyvinyl alcohol (PVA), partially saponified PVA, hydroxyethyl cellulose, carboxymethyl cellulose, methyl cellulose, polyacrylic acid, and polyvinylpyrrolidone.

Furthermore, a molecular weight modifier may be optionally used. Examples of the molecular weight modifier include mercaptans such as n-dodecyl mercaptan, octyl mercaptan, t-butyl mercaptan, thioglycolic acid, thiomalic acid, and thiosalicylic acid; sulfides such as diisopropylxanthogen disulfide, diethylxanthogen disulfide, and diethylthiuram disulfide; halogenated hydrocarbons such as iodoform; and diphenylethylene, p-chlorodiphenylethylene, p-cyanodiphenylethylene, and α-methylstyrene dimers.

The aqueous resin dispersion obtained by the above emulsion polymerization is used as a paint and a gluing agent for forming coating films or used for collecting solid polymers using a precipitant by a typical method. In other words, a polymer film is obtained by drying the obtained aqueous resin dispersion at ordinary temperatures or under heating if necessary. Furthermore, a solid polymer can be collected by, for example, adding an acid or a salt that has been used as a precipitant in the related art, performing stirring to precipitate a polymer, and performing filtration.

EXAMPLES

Hereafter, the present invention will be further described in detail based on Examples, but is not limited thereto. In structural formulae below, EO represents an oxyethylene group and PO represents an oxypropylene group.

Synthesis Example

Surfactant (a-1):

Into a reaction vessel equipped with a thermometer and a reflux tube, 230 g (1.0 mol) of styrenated phenol (mixture of monostyrenated phenol:distyrenated phenol:tristyrenated phenol=72:27:1), 40 g (1.0 mol) of NaOH, and 210 g of acetone were charged, and the internal temperature was increased to 40° C. under stirring. Then, 91 g (1.2 mol) of allyl chloride was added dropwise thereto over 1 hour. After completion of the dropwise addition, the temperature was further kept at 40° C. for 2 hours to cause a reaction. After the reaction product was filtered and the by-product NaCl was removed, acetone was removed under a reduced pressure to obtain an ally styrenated phenyl ether. Into an autoclave, 290 g of the obtained allyl styrenated phenyl ether was charged, and stirred at 200° C. for 5 hours. Then, 880 g (20 mol) of ethylene oxide was caused to react in the presence of a potassium hydroxide catalyst at a pressure of 1.5 kg/cm³ and a temperature of 130° C. to obtain a compound (surfactant (a-1)) represented by formula below.

[Chem. 8]

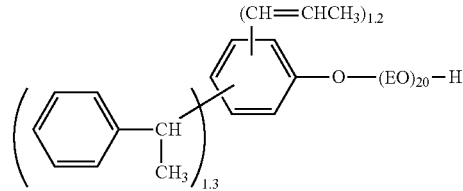

Surfactant (a-2):

A compound (surfactant (a-2)) represented by formula below was obtained by the same method as that of the surfactant (a-1), except that the amount of ethylene oxide was changed to 440 g (10 mol).

[Chem. 9]

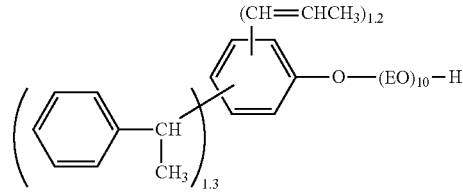

Surfactant (a-3):

A compound (surfactant (a-3)) represented by formula below was obtained by the same method as that of the surfactant (a-1), except that a mixture of 660 g (15 mol) of ethylene oxide and 174 g (3 mol) of propylene oxide was used instead of 880 g (20 mol) of ethylene oxide.

[Chem. 10]

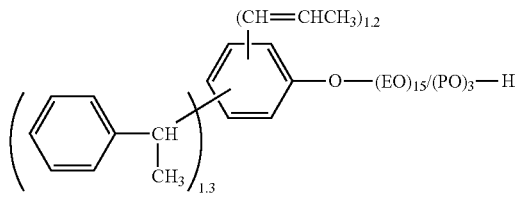

[Preparation of Aqueous Resin Dispersion]

A mixed monomer emulsion was prepared by mixing, with a homomixer, 123.75 g of styrene, 123.75 g of butyl acrylate, 2.5 g of acrylic acid, 7.5 g of a surfactant composition listed in Table 1, and 102.5 g of ion-exchanged water. In another reaction vessel equipped with a stirrer, a reflux condenser, a thermometer, a nitrogen inlet, and a dropping funnel, 122 g of ion-exchanged water and 0.25 g of sodium hydrogen carbonate were mixed with each other. To the reaction vessel, 36 g of the mixed monomer emulsion was added, and the temperature was increased to 80° C. and stirring was performed for 15 minutes. Subsequently, a mixture (aqueous solution) of 0.5 g of ammonium persulfate and 20 g of ion-exchanged water was added thereto and mixing was performed for 15 minutes. Then, the remaining mixed monomer emulsion was added dropwise thereto over 3 hours. After further mixing was performed for 2 hours, the temperature was decreased and the pH was adjusted to 8 using ammonia water to obtain an aqueous resin dispersion.

The surfactants b-1 to b-5, c-1, and c-2 in Table 1 are as follows.

b-1: polyoxyethylene styrenated phenyl ether ammonium sulfate (Product name: HITENOL NF-13, manufactured by DAI-ICHI KOGYO SEIYAKU CO., LTD.)

b-2: polyoxyethylene alkyl ether ammonium sulfate (alkyl group: C12 and C14 mixture, Product name: HITENOL LA-10, manufactured by DAI-ICHI KOGYO SEIYAKU CO., LTD.)

b-3: mixture of polyoxyethylene oleyl ether sodium sulfate and polyoxyethylene cetyl ether sodium sulfate (Product name: HITENOL W-2320, manufactured by DAI-ICHI KOGYO SEIYAKU CO., LTD.)

b-4: polyoxyethylene-1-(allyloxymethyl)alkyl ether ammonium sulfate (alkyl group: C11 and C13 mixture, Product name: AQUALON KH-10, manufactured by DAI-ICHI KOGYO SEIYAKU CO., LTD.)

b-5: polyoxyethylene nonylpropenylphenyl ether ammonium sulfate (Product name: AQUALON BC-20, manufactured by DAI-ICHI KOGYO SEIYAKU CO., LTD.)

c-1: isodecyl alcohol ethylene oxide (15 mol) adduct c-2: polyoxyethylene styrenated propenylphenyl ether ammonium sulfate (Product name: AQUALON AR-10, manufactured by DAI-ICHI KOGYO SEIYAKU CO., LTD.)

For the aqueous resin dispersion obtained by the emulsion polymerization, the polymerization stability, the chemical stability, and the water whitening resistance were evaluated. The evaluation methods are as follows.

[Polymerization Stability]

The aqueous resin dispersion was passed through a polyester mesh (200 mesh) to separate an aggregate generated during the emulsion polymerization. The filter residue was washed with water and then dried at 105° C. for 2 hours. The mass % of the filter residue relative to the solid content of the aqueous resin dispersion was determined from the mass of the dried filter residue, and evaluation was performed on the basis of the following criteria.

A: less than 0.1 mass %

B: 0.1 mass % or more and less than 1.0 mass %

C: 1.0 mass % or more

[Chemical Stability]

To 10 mL of the aqueous resin dispersion, 10 mL of a 2 mol/L, 3 mol/L, or 4 mol/L aqueous calcium chloride solution was added under stirring. The presence or absence of an aggregate was visually checked, and evaluation was performed on the basis of the following criteria.

A: An aggregate is not observed even when a 4 mol/L aqueous calcium chloride solution is added.

B: An aggregate is observed when a 4 mol/L aqueous calcium chloride solution is added.

C: An aggregate is observed when a 3 mol/L aqueous calcium chloride solution is added.

D: An aggregate is observed when a 2 mol/L aqueous calcium chloride solution is added.

[Water Whitening Resistance]

The aqueous resin dispersion was applied onto a glass plate so as to have a dry thickness of 120 μm, dried at 50° C. for 30 minutes, and then dried in an atmosphere of 20° C. and 65% RH for 48 hours. The obtained resin film was immersed in pure water at 25° C. The glass plate was placed on a 16-point printed text and the text was viewed through the resin film. The number of days taken until the text became unreadable was investigated, and evaluation was performed on the basis of the following criteria.

A: 15 days or longer

B: 10 days or longer and shorter than 15 days

C: shorter than 10 days

TABLE 1

|  | No. | Surfactant composition | | | Evaluation results | | |
|---|---|---|---|---|---|---|---|
|  |  | Surfactant (A) | Anionic surfactant (B) | A/B Mass ratio | Polymerization stability | Chemical stability | Water whitening resistance |
| Example | 1 | a-1 | b-1 | 3/7 | A | A | B |
|  | 2 | a-1 | b-2 | 4/6 | A | A | B |
|  | 3 | a-2 | b-3 | 2/8 | A | A | B |
|  | 4 | a-1 | b-4 | 3/7 | A | A | A |
|  | 5 | a-2 | b-5 | 3/7 | A | A | A |
|  | 6 | a-3 | b-5 | 2/8 | A | A | A |

TABLE 1-continued

| | No. | Surfactant (A) | Anionic surfactant (B) | A/B Mass ratio | Polymerization stability | Chemical stability | Water whitening resistance |
|---|---|---|---|---|---|---|---|
| Comparative Example | 1 | — | c-2 | — | A | D | A |
| | 2 | a-2 | — | — | C | A | A |
| | 3 | a-2 | c-2 | 3/7 | A | C | A |
| | 4 | c-1 | c-2 | 3/7 | A | B | C |
| | 5 | c-1 | b-5 | 3/7 | A | A | C |
| | 6 | c-1 | b-1 | 3/7 | A | A | C |

As is clear from Table 1, the chemical stability was poor in Comparative Example 1 in which only the anionic surfactant was used and the polymerization stability was poor in Comparative Example 2 in which only the surfactant (A) represented by the formula (1) was used. The chemical stability was poor in Comparative Example 3 in which the surfactant (A) represented by the formula (1) and an anionic surfactant having the same hydrophobic group as the surfactant (A) were used. The chemical stability and the water whitening resistance were poor in Comparative Examples 4 to 6 in which a nonionic surfactant different from the surfactant represented by the formula (1) and an anionic surfactant were used in combination.

In contrast, the three characteristics, namely, the polymerization stability, the chemical stability, and the water whitening resistance were excellent in Examples 1 to 6. In particular, the water whitening resistance was further improved in Examples 4 to 6 in which reactive surfactants were used in combination compared with in Examples 1 to 3. Thus, the three characteristics could be simultaneously satisfied at high levels.

INDUSTRIAL APPLICABILITY

The surfactant composition according to this embodiment can be used as, for example, an emulsifier for emulsion polymerization, an emulsifier for suspension polymerization, a resin modifier, and a fiber treatment agent. The aqueous resin dispersion obtained by using the surfactant composition as an emulsifier for emulsion polymerization or the like can be used as, for example, coating materials such as water-based paints, gluing agents, adhesives, and binders for paper processing.

The invention claimed is:

1. A surfactant composition, comprising:
   a surfactant (A) represented by the formula (1) below; and
   an anionic surfactant (B) having a hydrophobic group different from that of the surfactant (A),

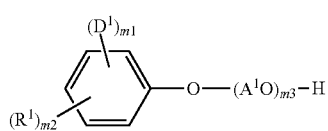
(1)

wherein $D^1$ is a polymerizable unsaturated group represented by the formula $D^1$-1 or $D^1$-2 below,

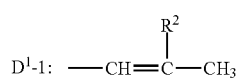

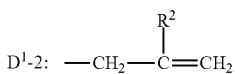

wherein $R^2$ is a hydrogen atom or a methyl group,
$R^1$ is one or two groups selected from the groups below, $R^1$: 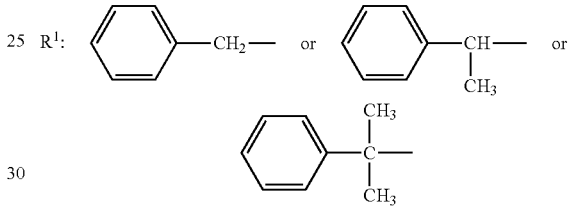

m1 and m2 are each 1 to 2 on average in the entirety of the surfactant (A),
$A^1$ is an alkylene group with 2 to 4 carbon atoms, and
m3 represents an average number of moles of the oxyalkylene group $A^1O$ and is in a range of from 1 to 100, and
wherein a mass ratio (A/B) of the surfactant (A) to the anionic surfactant (B) is from 4/6 to 2/8.

2. The surfactant composition of claim 1, wherein the anionic surfactant (B) has a polymerizable carbon-carbon unsaturated bond.

3. The surfactant composition of claim 1, wherein the anionic surfactant (B) has at least one hydrophobic group selected from the group consisting of a styrenated phenyl group, an alkyl group with 10 to 18 carbon atoms, an alkenyl group with 16 to 18 carbon atoms, a 1-(allyloxymethyl)alkyl group, and an alkylpropenylphenyl group.

4. The surfactant composition of claim 1, wherein the anionic surfactant (B) comprises at least one selected from the group consisting of a polyoxyalkylene styrenated phenyl ether sulfate, a polyoxyalkylene styrenated phenyl ether phosphate, a polyoxyalkylene styrenated phenyl ether carboxylate, a polyoxyalkylene styrenated phenyl ether sulfosuccinate, a polyoxyalkylene alkyl ether sulfate, a polyoxyalkylene alkyl ether phosphate, a polyoxyalkylene alkyl ether carboxylate, a polyoxyalkylene alkyl ether sulfosuccinate, a polyoxyalkylene alkenyl ether sulfate, a polyoxyalkylene alkenyl ether phosphate, a polyoxyalkylene alkenyl ether carboxylate, a polyoxyalkylene alkenyl ether sulfosuccinate, a polyoxyalkylene styrenated propenylphenyl ether sulfate, a polyoxyalkylene styrenated propenylphenyl ether phosphate, a polyoxyalkylene styrenated propenylphenyl ether carboxylate, a polyoxyalkylene styrenated propenylphenyl ether sulfosuccinate, a polyoxyalkylene alkylpropenylphenyl ether sulfate, a polyoxyalkylene alkylpropenylphenyl ether phosphate, a polyoxyalkylene alkylpropenylphenyl ether carboxylate, and a polyoxyalkylene alkylpropenylphenyl ether sulfosuccinate.

5. A method for producing an aqueous resin dispersion, the method comprising:
polymerizing a polymerizable compound in water in the presence of the surfactant composition of claim 1.

* * * * *